(12) United States Patent
Duff et al.

(10) Patent No.: US 10,035,136 B2
(45) Date of Patent: Jul. 31, 2018

(54) CATALYST FOR REDUCED NITROGEN OXIDE ($NO_x$) EMISSIONS IN AN OXODEHYDROGENATION PROCESS

(71) Applicant: TPC Group LLC, Houston, TX (US)

(72) Inventors: Joseph G. Duff, League City, TX (US); Jillian M. Horn, Decatur, GA (US); Michael O. Nutt, Pearland, TX (US); George S. Pappas, Galveston, TX (US)

(73) Assignee: TPC Group LLC, Houston, TX (US)

( * ) Notice: Subject to any disclaimer, the term of this patent is extended or adjusted under 35 U.S.C. 154(b) by 4 days.

(21) Appl. No.: 15/036,139

(22) PCT Filed: Mar. 25, 2015

(86) PCT No.: PCT/US2015/022429
§ 371 (c)(1),
(2) Date: May 12, 2016

(87) PCT Pub. No.: WO2015/148627
PCT Pub. Date: Oct. 1, 2015

(65) Prior Publication Data
US 2017/0036195 A1 Feb. 9, 2017

Related U.S. Application Data

(60) Provisional application No. 61/969,972, filed on Mar. 25, 2014.

(51) Int. Cl.
*B01J 23/78* (2006.01)
*B01J 23/80* (2006.01)
(Continued)

(52) U.S. Cl.
CPC ............. *B01J 23/80* (2013.01); *B01J 23/74* (2013.01); *B01J 23/745* (2013.01); *B01J 23/86* (2013.01);
(Continued)

(58) Field of Classification Search
CPC . B01J 23/80; B01J 23/74; B01J 23/745; B01J 23/86; B01J 23/8892; B01J 35/002; B01J 37/0207; B01J 37/0217; B01J 37/08
(Continued)

(56) References Cited

U.S. PATENT DOCUMENTS 3,450,787 A * 6/1969 Kehl .................. B01J 23/36
502/306
3,670,042 A * 6/1972 Croce .................. B01J 23/76
585/618
(Continued)

FOREIGN PATENT DOCUMENTS

GB 1 221 426 * 3/1971
WO 2010022923 A1 3/2010
(Continued)

OTHER PUBLICATIONS

"Prediction of Nitrogen Diffusivity in a-ferrite Based on Thermodynamics," Jae-gil Jung et al. Journal of Iron and Steel Research, International, 2015, 22(8), pp. 743-745. (Year: 2015).*

*Primary Examiner* — Patricia L. Hailey
(74) *Attorney, Agent, or Firm* — Michael W. Ferrell

(57) ABSTRACT

The present invention discloses a process to treat a ferrite based catalyst useful in the oxidative dehydrogenation of monololefins and diolefins which process includes a preheat step prior to use of the catalyst in the OXO-D reactor. The catalyst is preferably a zinc ferrite catalyst for the production of butadiene. It has been observed that substantially no nitrogen oxide emissions result from the use of this treated catalyst in the reactor unit during the oxidative dehydrogenation reaction.

13 Claims, 2 Drawing Sheets

TEMPERATURE RESOLVED MASS SPECTRA OF UNTREATED ZINC FERRITE (TOP TRACE), ZINC FERRITE TREATED TP 400°C IN AIR (MIDDLE TRACE), AND ZINC FERRITE TREATED TO 500°C IN AIR (BOTTOM TRACE). MASS 30 OXIDES OF NITROGEN IS MONITORED IN THIS REACTION TO SHOW NITRATE EVOLUTION FROM THE CATALYST WITH HEATING.

(51) Int. Cl.

| | |
|---|---|
| *B01J 37/08* | (2006.01) |
| *B01J 23/889* | (2006.01) |
| *B01J 23/74* | (2006.01) |
| *B01J 23/745* | (2006.01) |
| *B01J 23/86* | (2006.01) |
| *B01J 35/00* | (2006.01) |
| *B01J 37/02* | (2006.01) |
| *C07C 5/48* | (2006.01) |
| *C01G 49/00* | (2006.01) |
| *C07C 5/333* | (2006.01) |

(52) U.S. Cl.
CPC ......... *B01J 23/8892* (2013.01); *B01J 35/002* (2013.01); *B01J 37/0207* (2013.01); *B01J 37/0217* (2013.01); *B01J 37/08* (2013.01); *C01G 49/0063* (2013.01); *C07C 5/3332* (2013.01); *C07C 5/48* (2013.01); *B01J 23/78* (2013.01); *C01P 2002/82* (2013.01); *C01P 2006/80* (2013.01); *C07C 2523/02* (2013.01); *C07C 2523/04* (2013.01); *C07C 2523/80* (2013.01); *C07C 2523/86* (2013.01); *C07C 2523/882* (2013.01); *C07C 2523/883* (2013.01); *C07C 2523/889* (2013.01)

(58) Field of Classification Search
USPC .......................................................... 502/338
See application file for complete search history.

(56) References Cited

U.S. PATENT DOCUMENTS

| | | | | |
|---|---|---|---|---|
| 3,702,875 | A * | 11/1972 | Manning | B01J 23/74 502/304 |
| 3,751,512 | A * | 8/1973 | Woskow | B01J 23/42 502/213 |
| 3,951,869 | A * | 4/1976 | Baker | B01J 23/8892 502/324 |
| 4,083,884 | A | 4/1978 | Purdy | |
| 4,150,064 | A * | 4/1979 | Miklas | B01J 23/80 585/625 |
| 5,716,515 | A | 2/1998 | Innes | |
| 7,582,272 | B2 | 9/2009 | Glova et al. | |
| 2012/0059208 | A1* | 3/2012 | Mamedov | B01J 23/80 585/625 |

FOREIGN PATENT DOCUMENTS

| | | |
|---|---|---|
| WO | 2011127505 A1 | 10/2011 |
| WO | 2013148913 A1 | 10/2013 |

\* cited by examiner

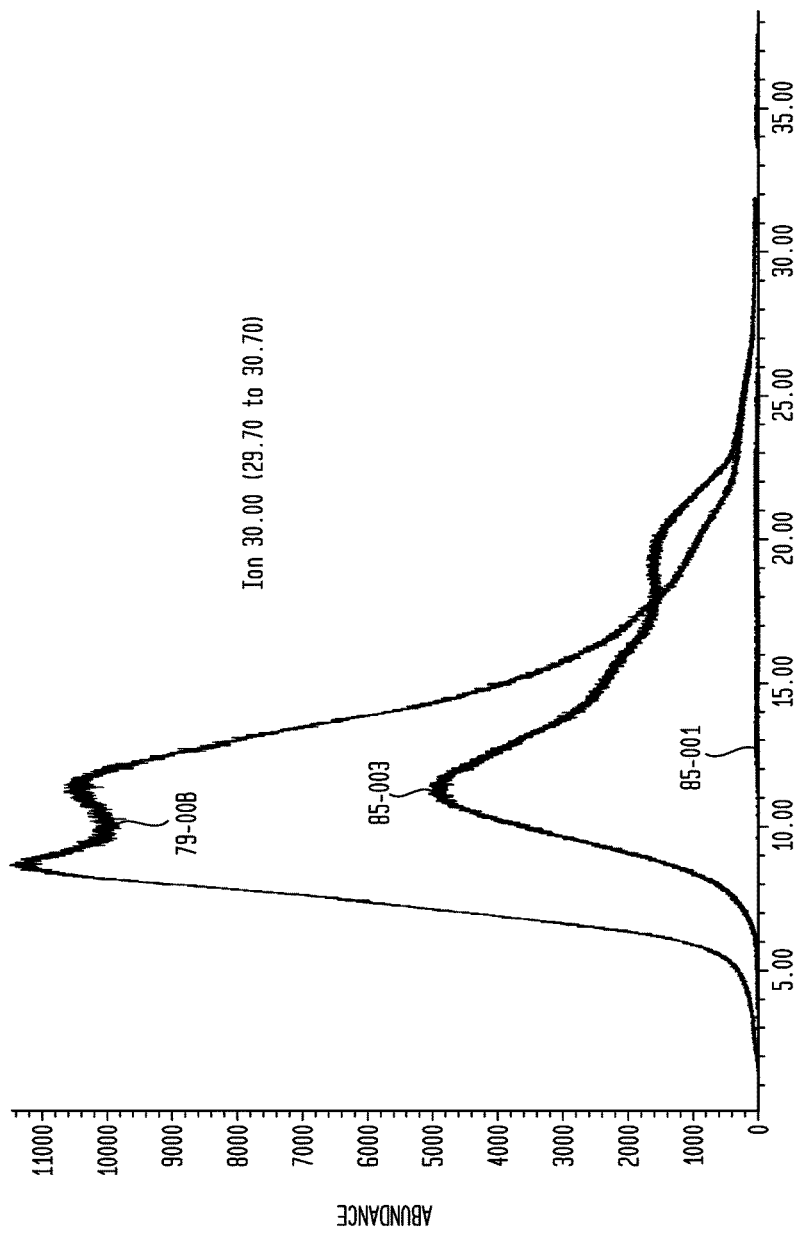

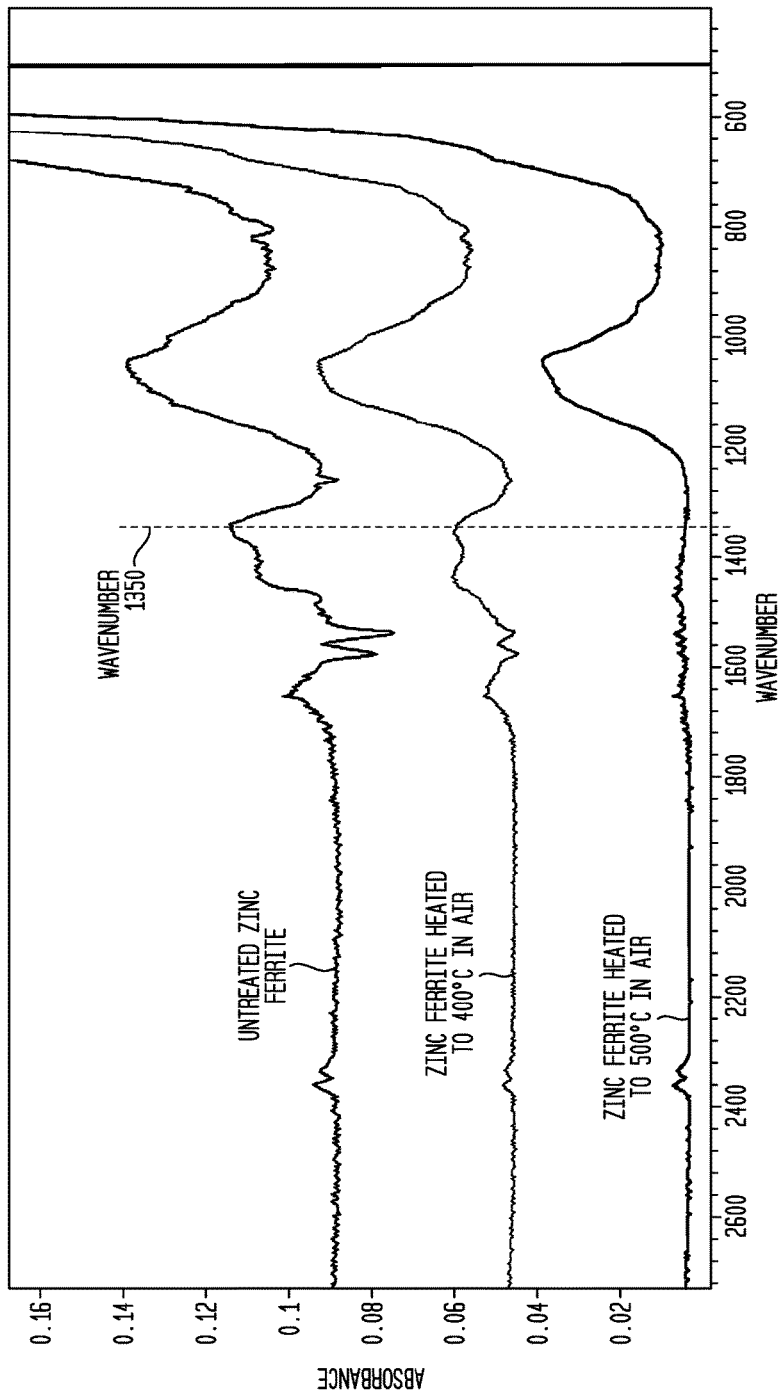

CATALYST FOR REDUCED NITROGEN OXIDE (NO$_x$) EMISSIONS IN AN OXODEHYDROGENATION PROCESS

CLAIM FOR PRIORITY

This application is based on International Application No. PCT/US2015/022429 filed Mar. 25, 2015 entitled "Catalyst for Reduced Nitrogen Oxide (NO$_x$) Emissions in an Oxodehydrogenation Process" which was based on U.S. Provisional Application Ser. No. 61/969,972, filed Mar. 25, 2014. The priorities of the foregoing applications are hereby claimed and their disclosures incorporated herein by reference.

TECHNICAL FIELD

The present invention is directed towards a preheat treatment of a ferrite, preferably zinc, catalyst and process for use in oxidative dehydrogenation of hydrocarbon. The resulting catalyst has reduced nitrogen oxide formations on start up in the reaction unit.

BACKGROUND

The present invention relates to the preheating treatment of a ferrite, preferably zinc ferrite, catalyst for use in oxidation reactions, and oxidative dehydrogenation ("OXO-D") of hydrocarbons, in particular for use in conversion of C1-C9 hydrocarbons, and more particularly, C3-C5 hydrocarbons. Further the invention relates to a composition of the catalyst found after the treatment step. The catalyst can be used for the conversion of butene to butadiene. As used herein, butene refers to both butene-1 and butene-2 molecules, and butadiene refers to 1,3 butadiene molecules.

During the startup of an oxidative dehydrogenation process of hydrocarbons employing traditional zinc ferrite catalyst having nitrate components, nitrogen oxides byproduct (NO and NO$_2$), commonly referred to as NO$_x$, is formed. If left within the reaction system, the NO$_x$ can react with butene/butadiene and create explosive nitrated compounds. In the past, traditional zinc ferrite, nitrated catalysts were employed in the OXO-D reactor, heated with air and/or steam and/or methane, and NO$_x$ components were released to the atmosphere untreated. Due to environmental concerns, releasing of nitrogen oxides is no longer acceptable without treatment. Due to the cost of equipment for NO$_x$ treatment among other reasons, a need exists to produce unsaturated hydrocarbons, in particular butadiene, with minimal to no NO$_x$ byproducts formed during the oxidation reaction.

Numerous patents and references exist describing heat treatment of catalysts for various reasons, such as regeneration, removal of coke/minimize fouling in a reaction system, or oxidation of the catalyst prior to use in a reactor, among other reasons. Often, in spite of treating the catalyst for removal of specific groups, the user must also deal with the handling issues of the catalyst and care of the catalyst to preserve its effectiveness (conversion/selectivity/yield or CSY performance), robustness, or thermal stability.

See WO 2011/127505 entitled "Vanadate Catalyst for Auto Exhaust Emissions"; EP 2 321 044 entitled "Silver Catalyst for Formaldehyde Preparation"; U.S. Pat. No. 7,582,272 entitled "A Method of Treating a Catalytic Reactor System Prior to Reactor Servicing"; U.S. Pat. No. 5,716,515 entitled "High Temperature Treatment of Reforming Catalyst With an Inert Gas"; PCT Application No. US 2013/034215 describes low emission OXO-D catalyst for butadiene production having improved controllability, and in situ heat processing.

U.S. Pat. No. 4,083,884 to Purdy describes a calcium oxide modified zinc ferrite oxidative dehydrogenation catalyst and use thereof for the production of butadiene. Calcium oxide is used therein as a modifier for the catalyst to suppress carbonyl compound formation during the butene to butadiene reaction. There is no mention of a nitrate-free catalyst or production of nitrogen oxide byproducts in the reaction.

U.S. Pat. No. 4,083,884 discloses activation of the catalyst in situ in reducing atmospheres at a temperature of about 1000° F. (cf Purdy, Col. 6, lines 24-33). During this process a nitrate based catalyst would release NO$_x$ into the OXO-D system. The NO$_x$, or nitrogen oxide byproducts, present safety hazards and thus need to be managed for both safety and environmental reasons.

Thus, in view of the formation of nitrogen oxides with the use of traditional ferrite-based catalyst, it would be preferable to find a catalyst or process for formation of butadiene without the NO$_x$ byproducts, yet having acceptable catalyst performance and handling during use.

A need exists for a catalyst which can perform at acceptable levels, be sufficiently robust for ease in handling, and also not produce harmful effects to the desired butadiene product or the environment.

SUMMARY OF INVENTION

The present invention discloses a preheat treatment of a catalyst prior to use in the reactor for an OXO-D reaction. This preheat treatment step was found to produce a heretofore not known composition having no oxides of nitrogen, as seen in previous Purdy catalysts, shown through IR by removal of nitrate antisymmetric stretching at approximately 1350 cm$^{-1}$ in FIG. 2. That is, the 1350 wavenumber peak is characteristic of nitrates in the catalyst.

Due to the environmental concern with nitrogen compounds during the OXO-D reaction, and their safety element, the resulting nitrate-free catalyst after heat treatment, yields minimal to no nitrogen compounds during use in the reaction zone, yet maintains its robust character when utilized.

The catalysts can be preheated to treat the catalyst outside the OXO-D system. Temperatures can range from about 300° C. to about 650° C., under inert gases, air, nitrogen and/or methane/natural gas for a period of about 5 minutes to about 360 minutes. Catalyst characteristics include reduced or no NO$_x$ formation during the hydrocarbon reaction process, and greater efficiency during start-up of the reaction process.

Other features and advantages will become apparent from the discussion which follows.

BRIEF DESCRIPTION OF DRAWINGS

The present invention is described in connection with the attached Figures, wherein:

FIG. 1 shows temperature resolved mass spectra of untreated and treated samples wherein mass 30 oxides of nitrogen are monitored to show nitrate evolution; and FIG. 2 shows IR spectra showing nitrate peak (1350 cm$^{-1}$) diminishing as a function of catalyst pretreatment with heat.

DETAILED DESCRIPTION

The invention is described in detail below with reference to the drawings and examples. Such discussion is for purposes of illustration only. Modifications within the spirit and scope of the present invention, set forth in the appended claims, will be readily apparent to one of skill in the art. Terminology used throughout the specification and claims herein is given its ordinary meaning except as more specifically defined; for example, time is calculated once the reactor reaches the allotted temperature.

It has been found that by preheating the catalyst outside of the reactor unit, or, before it is placed in the OXO-D reaction unit, surface nitrate groups may be removed. While the art is heavy with information of pretreatment with heat of a catalyst to remove undesirable components, it has been found that the removal of surface nitrate groups outside of the OXO-D reactor affords increased energy savings. The temperature of the reactor does not need to be raised as high for the removal of nitrogen groups, thus yielding energy and equipment (in wear and tear) savings. Further, the heat treated catalyst being devoid of surface nitrate groups will yield substantially no $NO_x$ emissions during use as an OXO-D catalyst. When the treated catalyst is used in the reaction unit to form butadiene, $NO_x$ are no longer formed. In addition to the environmental impact of this preheat pretreatment step, it is found to result in a more cost efficient catalyst because the reactor does not need to be heated as high during the reaction, thus saving energy. The invention discloses a process for the heat treatment of a zinc ferrite catalyst resulting in substantially no detectable surface nitrate group, said catalyst useful in a vapor phase process for oxidative dehydrogenation of monoolefins and diolefins having from about 2 to about 20 carbon atoms, and at least one

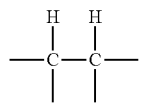

grouping.

The zinc ferrite catalyst comprising: $Zn(x)Fe(y)O(z)$, wherein x is about 0.1 to 2, y is about 0.3 to 12, and z is about 3 to 18, wherein further the ratio of y to x is about 2:1 to about 5:1. The catalyst also includes an alkali metal, and an alkaline earth element. The heat treatment comprises contacting the catalyst in an environment with a gas (inert gas, air, preferably $N_2$, methane or natural gas, steam, and the like) at a temperature of from about 350° C. to about 650° C., with a preferred range being about 400°-600° C., and most preferred range being about 450° to about 550° C. Any suitable atmosphere for heat-treatment may be used; a suitable atmosphere is an atmosphere which will not harm the catalyst under the conditions employed in heat treatment, nor present an explosion hazard or other hazardous condition. The time required for the preheat step will be dependent upon the temperature selected and generally being from about 5 minutes to about 360 minutes (6 hr). The extended period of time is generally associated with the lower temperature conditions. While longer heat times are not necessarily hurtful to the catalyst at lower temperatures, it may be commercially inefficient. The higher temperatures will allow for quicker removal of surface oxides of nitrogen which we refer to generally herein as nitrate groups. It has been found that temperatures as high as 650° C. did not damage the catalyst even after 2-3 hours of processing.

The heat treatment of the catalyst results in substantially no detectable surface nitrate groups. Herein, substantially no detectable surface nitrate groups means removal of at least 75% to about 98% by weight or by absorbance removal. More generally at least about 85% to about 95% of the groups are removed by weight or by absorbance, of the nitrate groups based on the initial catalyst.

Relative to the inert gases of interest, it is preferred to use pure oxygen, or a noble gas, or gas which is not reactive with the catalyst. Hydrogen is not preferred due to the possibility of a reduction reaction.

The equipment which may be employed includes a fixed bed, rotary kiln, or fluidized bed reactor (or reaction unit). A fixed bed is typically used in batch processes, while a fluidized bed or rotary kiln is employed for continuous mode of reaction. Ultimately, any equipment for the oxidation of olefins may be employed provided that it that does not damage the catalyst or make handling the catalyst in the equipment difficult. The point being that it is preferred to have ease in catalyst handling.

The high temperature treatment process of the present invention occurs prior to contacting the catalyst with a hydrocarbon feed. The ferrite-based catalyst is generally treated in a gaseous atmosphere in the temperature range of from about 300° C. to about 650° C. The preferred gas used is air, for reasons of availability and cost. Other inert gases, however, can be used, such as nitrogen, helium, argon, and krypton, or mixtures thereof. The use of purely an inert gas atmosphere for the high temperature treatment allows one to avoid the problems inherent in using a reducing gas such as hydrogen.

The gas entering the reactor should contain less than 100 ppmv water. It is preferred that it contain less than 10 ppmv water. In a commercial operation, the reactor effluent may be passed through a drier containing a desiccant or sorbent such as 4 A molecular sieves. The dried gas containing less than 100 ppmv water or, preferably, less than 10 ppmv water may then be recycled to the reactor. In the event a wetter gas is employed, one would need to upgrade the metallurgy and/or employ special handling techniques to avoid excessive corrosion. Dry gas helps to avoid corrosion issues and is accordingly preferred.

Because of the additional handling needed for the catalyst (i.e., first to preheat prior to use in the OXO D reaction, and then as an OXO D reaction catalyst), it is required that the catalyst maintain robustness and integrity to withstand transfer from one reactor to another for use.

Inert gases to employ include $N_2$, Ar, He, and Kr. Other gases which may be used include air (preferred due to cost), methane, and steam (anhydrous meaning non-condensing steam). Mixtures of the above mentioned gases may also be employed.

An advantage of the present invention is the savings in overall energy supplied to the unit due to preheating of the catalyst outside of an oxidative dehydrogenation reactor. Generally, the reactors are designed for low pressure drop so there is an energy cost associated with the low P drop. For a preheat treatment, a reactor does not need to be used, and one can utilize a more efficient heater than that associated with a reactor. A heater will require less btu's (energy) compared to a reactor used to preheat a catalyst. The rise in temperature for the entire heated area will require more energy in a reactor, than in a catalyst heater or oven.

The preferred combination of conditions for a batch reaction system involves use of a fixed bed reactor unit under nitrogen flow, at a temperature of about 500° C. for a duration of about 120 min, after reaching 500° C. The preferred combination of conditions for a continuous process involves use of a rotary kiln furnace, at a temperature of about 500° C., for duration of about 15 minutes and under an atmosphere of air.

To obtain the results of significantly reduced to no $NO_x$ emissions in the reactor; the treated catalyst must show substantially no surface nitrate groups when subjected to analytical testing. Testing methods may vary provided the nitrate group is ultimately monitored by some method. For example, the test may involve monitoring of the nitrate (oxides of nitrogen) peak (at wavelength 1350) with IR spectrometry; or alternatively, temperature resolved mass spectrometry may be employed for monitoring oxides of nitrogen on a subsample of material. The 30 MW mass spectrometry signal is characteristic of oxides of nitrogen evolving from the substrate.

While the invention is directed to ferrite catalyst, specific examples and description revolve around zinc ferrite catalyst. Preparation of the zinc or other ferrite catalyst may be by procedures known in the art. The subject invention is directed to the preheat step prior to use of the catalyst in the reactor. It is advantageous to conduct the pretreatment step outside of the reactor unit because of the energy savings observed by not employing the higher temperatures in the reactor. It has been found that after the heat treatment, the zinc catalyst of the study showed essentially no antisymmetric stretching of nitrate peak at 1350 $cm^{-1}$, when employing IR spectrometry. This catalyst was then placed in a reactor for the production of butadiene, and it was observed that no $NO_x$ was released from the reaction unit. The zinc ferrite catalyst comprised: $Zn(x)Fe(y)O(z)$, wherein x is about 0.1 to 2, y is about 0.3 to 12, and z is about 3 to 18, wherein further the ratio of y to x is about 2:1 to about 5:1, and also included calcium in the range of about 0.5 to about 5 weight percent as a nitrate salt before the catalyst has been treated in accordance with the preheat treatment, and after the preheat treatment contained about 0.17 to about 1.7% as oxide of the CaO.

The subject ferrite catalyst also contains alkali/alkaline earth metals. The metal used will cause the ratios to vary. Suitable alkali/alkaline metals include: Na, Mg, Ba, Cs, K, Ca, Rb, Sr.

Other than zinc, suitable metals include: Co, Ni, Cr; however, Cr is not as preferred due to the handling and toxicity issues involved.

The amount of Ca or other alkali or alkaline earth element employed is about 0.1 to 1.3 weight percent on dry basis based on total catalytic metal oxide weight (excluding any support or diluents), preferably about 1.0-1.3 weight percent on dry basis of said catalyst, and more preferably about 1.2-1.3 weight percent. If making a zinc ferrite catalyst, the amount of ZnO employed is about 20-40 weight percent on dry basis based on total catalytic metal oxide weight (excluding any support), preferably about 25-35 weight percent on dry basis of said catalyst, and more preferably about 28-30 weight percent. The amount of MnO employed is about 1-20 weight percent on dry basis based on total catalytic metal oxide weight (excluding any support), preferably about 2-10 weight percent on dry basis of said catalyst, and more preferably about 3-5 weight percent. The remaining amount of catalytic metal oxide in the catalyst is typically $Fe_2O_3$. The amount of iron is in the range of about 50 to 80 weight percent, preferably 60-70 weight percent, and more preferably about 63-68 weight percent. A $Fe_2O_3$/ZnO ratio of about 2.3 is desired. Testing was accomplished by traditional x-ray crystallography methods. U.S. Pat. No. 3,303,235 (Col. 6, lines 24-35) discloses x-ray diffraction and crystallography employed in the analysis of the catalyst, is herein incorporated by reference for this analytical information.

Traditional zinc ferrite catalysts can be made by various processes such as recited in U.S. Pat. No. 4,083,884 to Purdy, the disclosure of which is incorporated herein by reference. In particular, U.S. Pat. No. 4,083,884, at Col. 9, lines 40-50, recites mixing dry components to make a slurry of zinc ferrite mixture, calcine the slurry, crush the dry mixture, mix in a combination of phosphoric acid, calcium component, and optional binder, followed by shaping into granules and drying the granulated pellets.

Heat Treatment

The catalysts described above undergo a heat treatment prior to use outside of the oxidation or OXO-D reactor. Temperatures of the heat treatment can range from about 300° C. to about 650° C. under air, nitrogen, or steam, for a period of about 5 to about 360 minutes, or for a sufficient period of time so that all or substantially all of the surface nitrate compounds are removed from the catalyst, but before the performance of the catalyst is impacted. Benefits of the heat treatment can be seen in catalyst characteristics and if nitrate components are involved, then no $NO_x$ form during the hydrocarbon reaction process. It is desired to improve $NO_x$ elimination but not negatively affect the performance or integrity of the catalyst.

Still other features and advantages will become apparent from the present discussion.

Use of the Catalyst

The subject catalyst can be employed in the vapor phase process for oxidative dehydrogenation of monoolefins and diolefins, having from about 2 to about 20 carbon atoms, and at least one

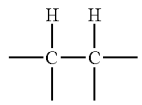

grouping.

The catalyst can be a traditional zinc ferrite structure as described in the art, pretreated as described above, followed by reduction in situ.

The organic compounds which can be treated according to the present process generally have 1 to 9 carbon atoms. The major portion of the stream can be saturated and/or unsaturated compounds and may comprise straight chain and/or branched compounds, similarly the desired compounds may be cyclic, acyclic or aromatic or mixtures of the foregoing. An illustrative, typical hydrocarbon feed in the input stream may contain, for example, mixed butenes (isobutene, 1-butene, cis-2-butene, trans-2-butene, 1,3-butadiene etc.) with acetylenes (such as, for example, methyl acetylene, ethyl acetylene, vinyl acetylene and the like), any butanes, mixed C5 hydrocarbons or other hydrocarbons. An example hydrocarbon stream would be the crude mixed butane/butadiene stream from ethylene cracker or the mid-process stream in butane/butadiene purification.

A preferred group of compounds are hydrocarbons having 1 to 9 carbon atoms, typically monoolefins and diolefins. A more preferred group of compounds are hydrocarbons having 2 to 8 carbon atoms, while a still more preferred group of compounds are hydrocarbons having 4 to 8 carbon atoms.

EXAMPLES

The following examples illustrate the discovery that high temperature pretreatment with an inert gas has a beneficial effect on the zinc ferrite catalyst, removing the surface nitrate groups. As demonstrated below, the $NO_x$ emission was below detectable limits, or a 100% reduction from the untreated catalyst.

Catalyst Characteristics

Two orthogonal analytical methods were used to determine essentially zero nitrate groups on the surface of the catalyst and essentially zero $NO_x$ release with the heat associated with reactor startup. Infrared spectroscopy indicated no nitrate groups present on the surface of the catalyst.

The following examples are only illustrative and are not intended to limit the invention. All percentages are by weight unless expressed otherwise.

Example 1—Data of Zinc and Nitrate-Free Catalyst Showing No $NO_x$ Formation

Due to transient formation of $NO_x$ in an oxidative dehydrogenation reaction, analysis of catalyst for $NO_x$ emissions can be analyzed by several methods including thermographic analysis (TGA) with suitable detection equipment (e.g. infrared or mass spectrometry) to detect $NO_x$ in the evolved gases.

A zinc ferrite catalyst was prepared in accordance with the U.S. Pat. No. 4,083,884 reference noted herein, particularly Example 4 where calcium was introduced via the calcium nitrate component which has been found to provide optimum performance for the catalyst. To test for the absence of surface nitrate groups, the catalyst was treated by standard ASTM E1252 including crushing the catalyst and inserting into an infrared spectra. Herein, IR BIO-RAD Excalibur Series FTS-3000 with ATR was employed. The orthogonal testing included mass spectrometry wherein an Agilent 5975 mass spectrometer was employed for gas detection.

Referring to FIG. 1, the temperature resolved mass spectra was run of untreated zinc ferrite, top trace (labelled 79-00B), zinc ferrite treated to 400° C. in air, middle trace (labelled 85-003), and zinc ferrite treated to 500° C. in air, lower trace, substantially undetectable line (labelled 85-001). Mass 30 (oxides of nitrogen) was monitored in this reaction to show nitrate evolution from the catalyst with heating for the three samples. It is appreciated from FIG. 1 that treatment to 400° C. in air is somewhat effective to reduce oxides of nitrogen, but that treatment to 500° C. in air removes substantially all of the oxides of nitrogen monitored over the course of the tests.

FIG. 2 shows infrared spectra detecting the characteristic nitrate peak (1350 wavenumbers) diminishing as a function of catalyst pretreatment. The top trace shows untreated zinc ferrite containing nitrate. Zinc ferrite heated to 400° C. in air, middle trace, shows a reduction of nitrate, while zinc ferrite heated to 500° C. in air shows no nitrate peak at 1350 wavenumber.

To ensure accuracy of the absence of nitrate groups, IR and mass spectrometer testing were performed several times to compare the data and ensure the spectrometers were functioning properly in a standard and routine fashion and providing consistent results. After receipt of the initial confirmation with orthogonal testing, one can use just one analytical test method to confirm the absence of nitrate groups. The catalyst was tested before and after the heat treat and the appropriate peak was monitored. It was found that with mass spectrometry, one can have different components in the system cracking at the same mass. However, no other peaks were offgassed from the mass spectrometer. The orthogonal testing was done nonetheless for ensurance of accuracy. For further details see IR reference: Goebbert, D. J.; Garand, E.; Wende, T.; Bergmann, R.; Meijer, G.; Asmis, K. R.; Neumark, D. M. *J. Phys. Chem. A* 2009, 113, 7584.

The zinc ferrite catalyst was heated to 500° C. in air and showed a selectivity of 93.5% (mole) and conversion of 80.0% (mole) when utilized in the OXO-D reactor.

It can be inferred that if the catalyst does not contain nitrogen compounds, no $NO_x$ will be formed on the catalyst, or in the reactor.

To ensure no damage to catalytic activity, performance testing of the resulting catalyst were performed on a lab scale oxidative dehydrogenation unit. The equipment used was similar to the one described in the aforementioned U.S. Pat. No. 4,083,884. The reactor was a 24" long, 1" I.D. stainless steel tube inserted in a 3100 watt furnace having three separate temperature control elements. The upper 8" serve as a steam super heater. The hydrocarbon feed was injected into the super heated steam prior to the steam entering a catalyst bed of about 10" length with inert support on top and bottom of the bed to fill the reactor. The effluent was sampled after cooling the outlet stream and condensing the water. Analyses were by gas chromatographic methods.

The output stream contains hydrogen. The steam/hydrocarbon (hydrocarbon=HC) ratios mol/mol are generally about 1-25 respectively, preferably being about 2 to 15 steam/HC, more preferably being about 3 to 8, and still more preferably about 3-5 steam/HC. The mix of hydrocarbon and steam ("the input stream") is run over a bed of the catalyst as described above at a targeted liquid hourly space velocity ("LHSV") based solely on the hydrocarbon feed. The targeted LHSV is generally in the range of 1-8, preferably 2-6 and more preferably 3-5. The temperature of the bed is controlled in the range about 250-900° C. (480-1650° F.) generally, about 315-760° C. (600-1,400° F.) preferably, about 480-650° C. (900-1,200° F.) more preferably and about 480-540° C. (900-1000° F.) typically, by adjusting the steam temperature and/or providing external heat to the system. The pressure of the bed is controlled at about 0-2.1 MPa (0-300 psia) generally, about 0.014-1.4 MPa (2-200 psia) preferably, about 0.07-0.35 MPa (10-50 psia) more preferably and about 0.1-0.11 MPa (14-16 psia) typically, by controlling off-gas pressure. The exit or effluent gas is cooled to condense water away from the hydrocarbons. The recovered hydrocarbon mix is sent for further purification to separate the hydrocarbons from the CO, $CO_2$ and hydrogen as needed.

Performance testing of the resulting catalyst was performed on a lab scale OXO-D unit. The equipment used was similar to that described in U.S. Pat. No. 4,083,884. The reactor was a 24" long, 1" I.D. stainless steel tube inserted in a 3100 watt furnace having three separate temperature control elements. The upper 8" serve as a steam super heater. The hydrocarbon feed was injected into the super heated steam prior to the steam entering a catalyst bed of about 10" length with inert support on top and bottom of the bed to fill the reactor. The effluent was sampled after cooling the outlet stream and condensing the water. Analyses were by gas chromatographic methods. It was found that the C/S/Y of the treated catalyst was within 1% of the untreated catalyst.

In typical runs, the hydrocarbon mix was vaporized and mixed with steam at a desired steam/hydrocarbon ratio. This input stream was run over the catalyst bed at a targeted LHSV based solely on the hydrocarbon feed composition. Temperature of the bed was controlled by adjusting the steam temperature and/or providing external heat to the system. The exit gas was cooled to condense water away from the hydrocarbons and analyzed.

A pretreated zinc ferrite catalyst was employed under the following reaction conditions:

approximately: 125 ml catalyst; high purity B1 as feed (99+%), LHSV 2;
O2/steam/HC=0.55/12/1, with O2 as air;
Inlet temp=650° F.
Outlet temp=1050° F.;
Catalyst reduction temp=1000 F/H2. Time=120 minutes The data herein demonstrate that use of the nitrate-free zinc ferrite catalyst results in no discernible nitrogen oxide byproduct formation, making the gaseous streams from the butene reaction acceptable for venting to the atmosphere without any adverse environmental effects.

Even though the foregoing Example illustrates the lack of nitrogen oxide formation, the present invention has other advantages. For example, the lack of $NO_x$ formation allows for venting the gas to the atmosphere and not having to pre-treat resulting in energy and equipment savings. The equipment savings stems from further use that is not necessary compared when a nitrated catalyst is used. The nitrate free catalyst avoids damage to equipment typically caused by nitrated catalyst in the form of corrosion.

As can be seen, the instant invention affords a novel process to produce butadiene without nitrogen oxide byproducts. The novel process for pretreating the catalyst does not negatively affect the production of desired mono- and diolefinic compounds, in particular butadiene.

While the invention has been described in detail, modifications within the spirit and scope of the invention will be readily apparent to those of skill in the art. In view of the foregoing discussion, relevant knowledge in the art and references discussed above in connection with the Background of the Invention, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A process for producing a ferrite catalyst suitable for use in an oxydehydrogenation process, comprising preparing a calcined ferrite catalyst formulated with nitrate, and then pre-treating the calcined ferrite catalyst formulated with nitrate with a heat pre-treatment prior to use in an oxydehydrogenation process, wherein the calcined ferrite catalyst formulated with nitrate is heat-treated at a temperature range of about 300° C. to about 650° C., for a time range of about 5 minutes to about 360 minutes (6 hr), in at least one of a fixed bed, rotary kiln, or fluidized bed reactor, under a suitable atmosphere, wherein the heat pre-treated calcined ferrite catalyst formulated with nitrate has a reduced level of surface nitrate groups as compared with the calcined ferrite catalyst formulated with nitrate prior to the heat pre-treatment.

2. The process of claim 1, wherein the temperature range of the heat pre-treatment is from about 400 to about 600° C.

3. The process of claim 2, wherein the temperature range of the heat pre-treatment is about 450-550° C.

4. The process of claim 1 including carrying out the heat pre-treatment for a time period of about 5 to about 60 min.

5. The process of claim 1, wherein analytical testing is conducted on the resulting heat pre-treated calcined ferrite catalyst formulated with nitrate and comprises IR spectrometry and the characteristic nitrate peak at 1350 $cm^{-1}$ is monitored.

6. The process of claim 1 wherein, analytical testing is conducted on the resulting heat pre-treated calcined ferrite catalyst formulated with nitrate modified catalyst and comprises mass spectrometry and oxides of nitrogen are monitored.

7. The process of claim 1, wherein the heat pre-treatment of the calcined ferrite catalyst formulated with nitrate is carried out with a fixed bed provided with nitrogen flow, at a temperature of about 500° C., for a time period of about 120 min after reaching 500° C. in the fixed bed reactor.

8. The process of claim 1, wherein the heat pre-treatment of the calcined ferrite catalyst formulated with nitrate is carried out in a rotary kiln furnace under air flow, at a temperature of about 500° C., for a time period of about 15 min, after reaching 500° C. in the furnace.

9. The process of claim 1, wherein the heat pre-treatment of the calcined ferrite catalyst formulated with nitrate is effective to remove about 75%-98% by weight of the surface nitrate groups.

10. The process of claim 8, wherein the heat pre-treatment of the calcined ferrite catalyst formulated with nitrate is effective to remove about 85%-95% by weight of the surface nitrate groups.

11. The process of claim 1, wherein heat pre-treatment of the calcined ferrite catalyst formulated with nitrate is carried out under an atmosphere selected from inert gas, air, nitrogen, methane, natural gas, steam and suitable mixtures thereof.

12. The process of claim 1, wherein heat pre-treatment of the calcined ferrite catalyst formulated with nitrate is carried out in air.

13. The process of claim 1, wherein the heat pre-treated calcined ferrite catalyst formulated with nitrate is substantially free of detectable surface nitrate groups.

* * * * *